(12) United States Patent
Hagino et al.

(10) Patent No.: US 8,841,638 B2
(45) Date of Patent: Sep. 23, 2014

(54) PARTICLE BEAM THERAPY SYSTEM

(75) Inventors: Takeshi Hagino, Chiyoda-ku (JP); Taizo Honda, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/116,203

(22) PCT Filed: Jul. 21, 2011

(86) PCT No.: PCT/JP2011/066548
§ 371 (c)(1),
(2), (4) Date: Nov. 7, 2013

(87) PCT Pub. No.: WO2013/011583
PCT Pub. Date: Jan. 24, 2013

(65) Prior Publication Data
US 2014/0088336 A1    Mar. 27, 2014

(51) Int. Cl.
*G21K 5/04* (2006.01)

(52) U.S. Cl.
USPC ................. 250/492.3; 250/492.1; 250/396 R; 600/1

(58) Field of Classification Search
USPC .......... 600/1, 2, 3, 4, 5; 250/396 R, 397, 398, 250/396 ML
See application file for complete search history.

(56) References Cited

U.S. PATENT DOCUMENTS

| | | | |
|---|---|---|---|
| 2006/0065836 A1 | 3/2006 | Tsuchiya et al. | |
| 2006/0076515 A1 | 4/2006 | Matsuda et al. | |
| 2008/0029705 A1 | 2/2008 | Tsuchiya et al. | |
| 2009/0242789 A1 | 10/2009 | Tachikawa | |
| 2010/0171047 A1 | 7/2010 | Matsuda et al. | |
| 2010/0288946 A1 | 11/2010 | Honda et al. | |
| 2011/0218429 A1 | 9/2011 | Harada et al. | |
| 2013/0274538 A1* | 10/2013 | Yamada et al. | .................. 600/1 |

FOREIGN PATENT DOCUMENTS

| | | | |
|---|---|---|---|
| JP | 2006-128087 A | 5/2006 | |
| JP | 2007-268031 A | 10/2007 | |
| JP | 2009-236867 A | 10/2009 | |

(Continued)

OTHER PUBLICATIONS

International Search Report (PCT/ISA/210) mailed on Aug. 30, 2011, by the Japanese Patent Office as the International Searching Authority for International Application No. PCT/JP2011/066548.

(Continued)

*Primary Examiner* — Nicole Ippolito
(74) *Attorney, Agent, or Firm* — Buchanan Ingersoll & Rooney PC

(57) ABSTRACT

An particle beam therapy system comprises a scanning electromagnet for scanning a particle beam which travels in a vacuum duct so as to irradiate an irradiation object and an irradiation unit comprising a beam outlet window, wherein the irradiation unit is configured such that the vacuum duct can be divided by a flange surface which is provided at a position closer to an irradiation object than a scanning electromagnet, in a case where a vacuum duct for a scanning irradiation method which is provided at a position closer to an irradiation object than the flange surface is moved so as not to overlap a beam line of the particle beam, a ride filter for a broad beam irradiation method can be provided at space where the vacuum duct for a scanning irradiation method was provided before it was moved.

6 Claims, 7 Drawing Sheets

(56) References Cited

FOREIGN PATENT DOCUMENTS

| | | |
|---|---|---|
| JP | 2010-017365 A | 1/2010 |
| JP | 4393581 B1 | 1/2010 |
| WO | WO 2009/139037 A1 | 11/2009 |

OTHER PUBLICATIONS

Weber et al., "Design and construction of a ripple filter for a smoothed depth dose distribution in conformal particle therapy", Phys. Med. Biol. 44, 1999 (month unknown), pp. 2765-2775.

\* cited by examiner

A – A SECTIONAL VIEW

PARTICLE BEAM THERAPY SYSTEM

TECHNICAL FIELD

This invention relates to particle beam therapy system in which a particle beam is applied such as performing cancer treatment by irradiating a particle beam.

BACKGROUND ART

Irradiation method of particle beam therapy system is divided broadly into two methods. That is, a broad irradiation method in which a beam is irradiated into whole of patient's affected area simultaneously and a scanning irradiation method in which a beam is scanned and irradiated. In order to realize a broad beam irradiation method and a scanning irradiation method, equipment and controlling methods which are suited for the irradiation methods are required.

Regarding irradiation apparatuses which are used for conventional scanning irradiation methods, in order to increase accuracy of irradiation position of patient's affected area, a configuration, in which a vacuum region or a region of gas which is lighter than air such as helium is secured and scattering of a beam is suppressed so as to reduce a size of a beam, has been proposed. A part in which a vacuum region or a gas region is secured is indicated as a chamber (beam transport chamber, gas chamber, etc.), or a duct (vacuum duct, etc.). In order to irradiate a beam having a small spot size, an irradiation apparatus which is used for a scanning irradiation method should have a configuration such that a scattering of a beam in a path, before an irradiation object (isocenter) which is caused by air has to be suppressed. Therefore, according to the configuration, right up to an irradiation position is a vacuum region or a gas region, and substances which scatter a beam including an isolation window (beam outlet window) in the region are arranged in the most downstream which is close to an irradiation object.

Further, regarding a broad beam irradiation method, equipment including a spread out Bragg peak forming filter, a collimator and a bolus should be installed in an irradiation apparatus. By using the equipment, an energy distribution of a beam and a beam shape are formed so as to form a particle beam irradiation filed which is suited to a shape of an affected area. According to a broad beam irradiation method, an irradiation field is formed by scattering a particle beam; therefore, it is not necessary to suppress a spot size to be small. Consequently, unlike an irradiation system apparatus which is used for a scanning irradiation method, it is not required to have the configuration such that a vacuum duct is arranged right up to an irradiation object so as to suppress a scattering caused by air in an irradiation apparatus.

As above mentioned, a configuration of a scanning irradiation method and that of a broad beam irradiation are different, therefore, it is difficult to realize a plurality of irradiation methods at one irradiation unit. These irradiation methods have different characteristics and depending on an irradiation part and a shape of an affected part, suited irradiation method is different. As a configuration for realizing a scanning irradiation method and a broad beam irradiation method, Patent Document 1 discloses a configuration, that is, a plurality of treatment rooms are provided, in some of the treatment rooms, an irradiation apparatus of a scanning irradiation method is installed, and in other treatment rooms, an irradiation apparatus of a broad beam irradiation method is installed. However, according to the above-mentioned method, an irradiation unit is required for each irradiation method, therefore, cost as a whole of system is increased. As a configuration for resolving the above-mentioned points, Patent Document 2 discloses a configuration, that is, a gas chamber for suppressing scatter of a particle beam is made to be extendable in the beam traveling direction, and in space which is made by contracting the gas chamber, equipment which is necessary for a broad beam irradiation are inserted so as to enable to realize a broad beam irradiation in the same irradiation unit.

PRIOR ART DOCUMENTS

Patent Document

Patent Document 1: JP 2007-268031A
Patent Document 2: JP 2010-17365A

Non-Patent Document

Non-Patent Document 1: "Design and construction of a ripple filter for a smoothed depth dose distribution in conformal particle therapy", Uli Weber and Gerhard Kraft, Phys. Med. Biol. 44 (1999) 2765-2775

DISCLOSURE OF THE INVENTION

Problems to be Solved by the Invention

Here, a spread out Bragg peak forming filter (hereinafter, will be referred to as a ridge filter) will be described. A ridge filter has a configuration such that is a necessary number of a bar ridge which is generally made of aluminum, brass, etc. and has a mountain-shaped cross-section are arranged so as to form an irradiation field. Regarding the ridge filter in order to obtain a flat spread out Bragg peak region, processing in several hundred micro meter to several ten micro meter order accuracy is required to form an inclined plane of the bar ridge. Therefore, it requires extremely long time (=cost) to manufacture a bar ridge having a long depth and height. Consequently, it is preferable such that a size of a ridge filter (Length: L, height: h) is small and pitch: $\lambda$ of bar ridges is large. In order to make a size of a ridge filter to be small, it is necessary to arrange a ridge filter itself apart from an irradiation object as far as possible. Further, in order to make a pitch: $\lambda$ of bar ridges to be large, it is necessary to arrange a ridge filter apart from an irradiation object. In Non-Patent Document 1, the above-mentioned relationship between a distance to an irradiation object and a pitch of bar ridges was described in detail.

Here, a problem regarding the configuration which was cited in Patent Document 2 will be described. According to the configuration disclosed in Patent Document 2, equipment which is used for a broad beam irradiation method is inserted in space which is made by contracting a gas chamber. However, in a case where a telescopic gas chamber is used, according to the configuration of the gas chamber, even where a gas chamber is contracted at a maximum, an area which is occupied by the gas chamber is not zero. Therefore, the gas chamber is positioned on a beam line. In order to reduce the size, Patent Document 2 proposes a telescopic mechanism of a cylindrical gas chamber in which the cylindrical gas chamber is divided by some sections so as to make outer shape to be larger toward downstream. However, in order to shorten a length of a gas chamber in a beam direction when the gas chamber is contracted, it is necessary to increase a number of sections for dividing. As the number of dividing increases, an outer shape of the gas chamber becomes extremely larger than a size which is necessary for passing a beam. Therefore, it is necessary for the configuration for inserting equipment which is used for a broad beam irradiation to arrange in a position having no interference with the gas chamber. Consequently, a distance which is necessary for switching of equipment becomes longer. In a case where a vacuum bellows, etc. is used in stead of a gas chamber is used, the same problem is generated. In a case where a vacuum bellows is used, it is considered such that the condition becomes worse than a case where a gas chamber is used. (In a case of a vacuum bellows, even when a bellows is contracted, the length is substantially half of full length.)

Because of the above-mentioned reason, according to equipment layout of Patent Document 2 when a broad beam irradiation is performed, a position of a ridge filter is extremely apart from a scanning electromagnet by an installation space of a gas chamber. As above mentioned, it is necessary to keep a distance between a ridge filter and an irradiation object, as a result, large space for arranging equipment which is necessary for irradiation is required.

This invention relates to a particle beam therapy system which realizes a plurality of irradiation methods by one irradiation nozzle in a particle beam therapy system which is used for cancer treatment. In order to solve the above-mentioned problems of conventional apparatus, this invention aims to provide a particle beam therapy system which can use a ridge filter which can be manufactured easily even when space between a scanning electromagnet and an irradiation object is small.

Means for Solving the Problems

According to this invention, in a particle beam therapy system comprising a scanning electromagnet for irradiation an irradiation object by scanning a particle beam which travels in a vacuum duct, and an irradiation unit having a beam outlet window from which a particle beam comes out from a vacuum duct to the atmosphere, wherein the irradiation unit has the configuration such that a vacuum duct is provided which can be divided by a flange surface at an irradiation object side than a scanning electrode, in a case where a vacuum duct for a scanning irradiation method which is provided at an irradiation object side than a flange surface is moved so as not to overlap with a beam line of a particle beam, a ridge filter for a broad beam irradiation method can be provided in space which is on a beam line of a particle beam and where the vacuum duct for a scanning irradiation method was provided before it was moved.

Advantage of the Invention

According to a particle beam therapy system of this invention, when equipment configuration is switched from that of a scanning irradiation method to that of a broad beam irradiation method, a ridge filter which is required for a broad beam irradiation method can be provided in the vicinity of a scanning electromagnet, therefore, a ridge filter, which can be manufactured easily even in a case where space from a scanning electromagnet to an irradiation object is small, can be used.

EMBODIMENTS FOR CARRYING OUT THE INVENTION

Embodiment 1

Figure 1:
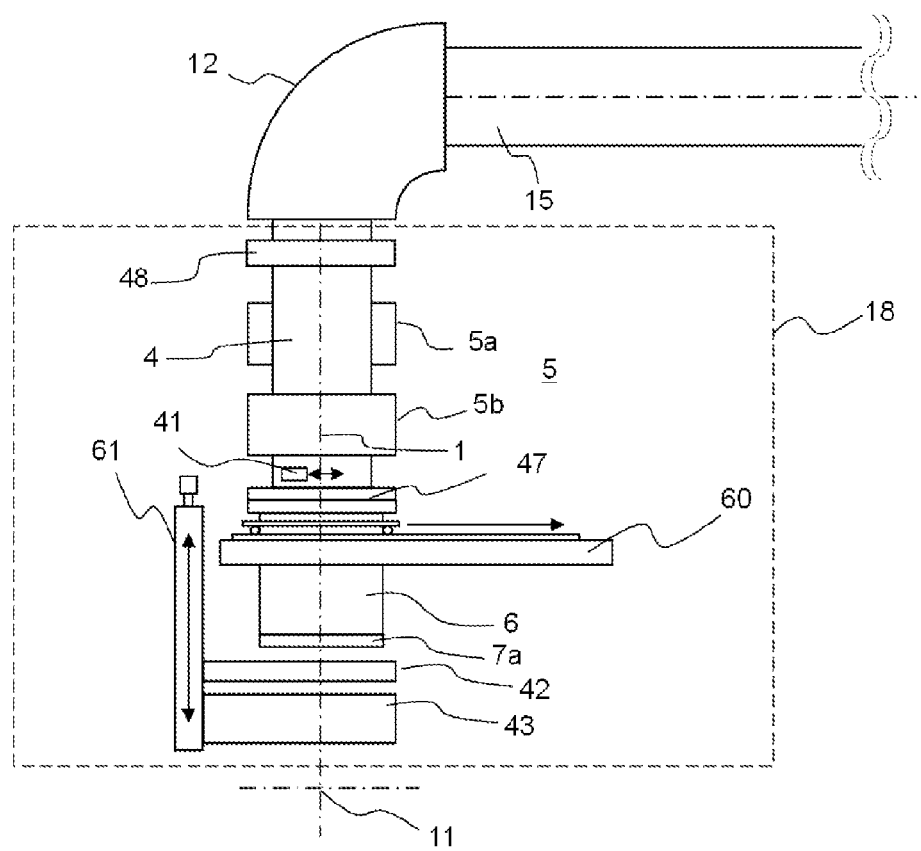
FIG. 1 is a front view showing a configuration of an irradiation unit which is a main unit of a particle beam therapy system in a case of a scanning irradiation method according to Embodiment 1 of this invention.
Figure 2:
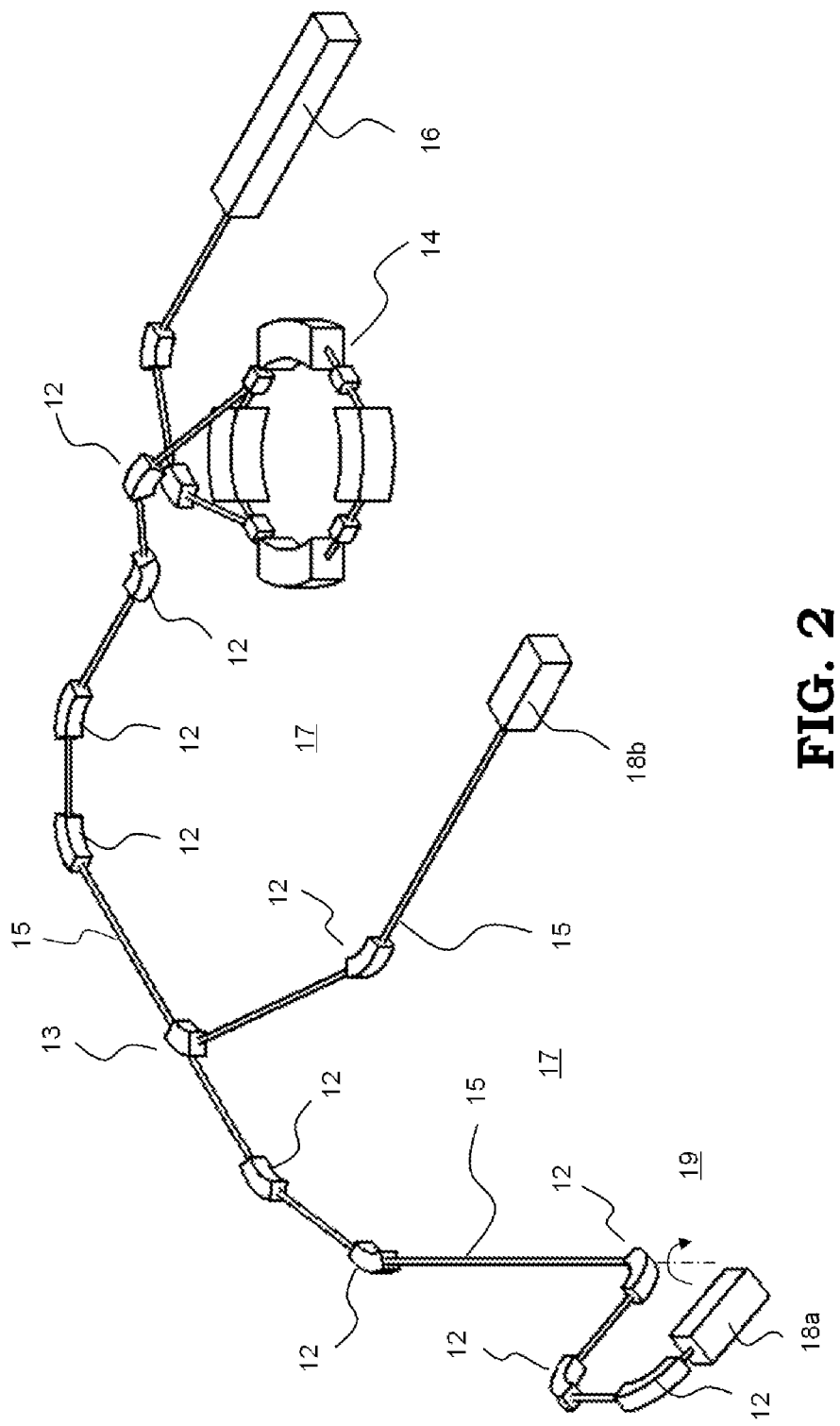
FIG. 2 is a schematic bird's-eye view showing an example of whole configuration of a particle beam therapy system to which this invention is applied.

FIG. 1 is a front view showing a configuration of an irradiation unit which is a main unit of a particle beam therapy system according to Embodiment 1 of this invention. FIG. 2 is a schematic bird's-eye view showing an example of whole configuration of a particle beam therapy system to which this invention is applied. In FIG. 2, a particle beam which is generated and pre-accelerated by a pre-accelerator 16 enters an accelerator (syncrotron) 14 so as to be accelerated to be necessary beam energy, and is extracted from an extracting deflector to a beam transport unit 17, reaches an irradiation unit 18 and irradiates an affected part of a patient which is an irradiation object. The beam transport unit 17 comprises a bending electromagnet 12, 13 and a vacuum duct 15, etc. In FIG. 2, at a position of the bending electromagnet 13, a beam transport system is branched, and one of the beam transport system connects to a rotating gantry 19. A part of the beam transport unit 17 and an irradiation unit 18a are mounted on the rotating gantry 19. By rotating the rotating gantry 19, an irradiation direction of the irradiation unit 18a can be changed. An irradiation unit 18b which is connected to other part of the branched beam transport system is not mounted on a rotating gantry, however, the configuration of the irradiation unit 18a and that of the irradiation unit 18b are basically same. Here, the irradiation units 18a and 18b are referred to collectively as the irradiation unit 18.

FIG. 1 shows the configuration in a case where a scanning irradiation method is performed. In FIG. 1, a particle beam which is extracted from the accelerator 14 is transported in the vacuum duct 15. In the irradiation unit 18, the particle beam passes through a vacuum duct 4 which secures a vacuum region and is communicated and a vacuum duct for a scanning irradiation method 6. And then, the particle beam comes out from a beam outlet window 7a to the atmosphere so as to irradiate an affected part which is an irradiation object. In FIG. 1, only an isocenter 11 which is a reference position of an affected part is shown. A particle beam scans an irradiation object with scanning electromagnets 5a and 5b (which are collectively referred to as a scanning electromagnet 5). The irradiation unit 18 comprises a vacuum duct transfer mechanism 60 for evacuating the vacuum duct for a scanning irradiation method 6 from a beam line 1 (a center of the beam line is indicated by reference note 1 with alternate long and short dash line), in order to switch a configuration of equipment arrangement of a scanning irradiation method to that of equipment arrangement of a broad beam irradiation method, a connection flange surface 47 with the vacuum duct 4, a gate valve 48 of the vacuum duct 4 for dividing a vacuum region just before the scanning electromagnet 5 and a scatterer 41 for scattering a particle beam in accordance with an irradiation field. Further, the irradiation unit 18 comprises a ridge filter 42 for spreading out Bragg peak of a particle beam in a depth direction and a range shifter 43 for adjusting a range of a particle beam. Here, the ridge filter 42 and the range shifter 43 are attached to a ridge filter transfer mechanism 61 so as to be able to transfer to a direction which is parallel with a beam line 1.

Next, operation will be described. In a case where an irradiation is performed by a scanning irradiation method by a particle beam therapy system according to EMBODIMENT 1, in order to reduce a spot size of a beam at a beam irradiation position by suppressing scattering of a particle beam as far as possible, the particle beam therapy system has the configuration such that a vacuum duct is arranged right up to a beam irradiation position. Here, a scatterer 41 is not required, therefore, the scatterer 41 is made to evacuate at a side of the beam line 1. In a case where a particle beam is a proton beam, in a scanning irradiation method, a ridge filter 42 is not required, however, in other particle beams, in some cases, a ridge filter is used for enlarging slightly an energy width. For example, in a case of heavy particle beam such as a carbon beam, a Bragg peak width is extremely sharp in comparison with that of a proton beam. Therefore, in order to reduce an irradiation time, in some cases, a ridge filter is used for forming a spread out Bragg peak (SOBP) having a certain size (several mm) so as to irradiate to a certain depth width in one scanning. However, in this case, the ridge filter is for spreading a width of a SOBP to be several mm, and a height of bar ridges may be shorter than a width of the SOBP. Even in a case where an arrangement position is not far from an irradiation object, a ridge filter, which can be manufactured easily than a ridge filter for broad beam, can be used. Further, a reach depth of a particle beam (range distance) is determined by energy of a particle beam; therefore, it is required to change energy of a particle beam so as to change a range distance of an energy beam. When energy is changed only by adjusting energy of an accelerator, it takes time for switching energy. Therefore, in some cases, a range shifter for reducing energy of a particle beam is used so as to change energy of a particle beam. A particle beam may be scattered by a range shifter. When the above-mentioned is taken into account, it is preferable such that a range shifter is arranged at a downstream side as far as possible, that is, at a position as close as possible to an irradiation object. Consequently, in a case where the ridge filter 42 or the ridge shifter 43 is used, an arrangement shown in FIG. 1 is preferable.

Figure 3:
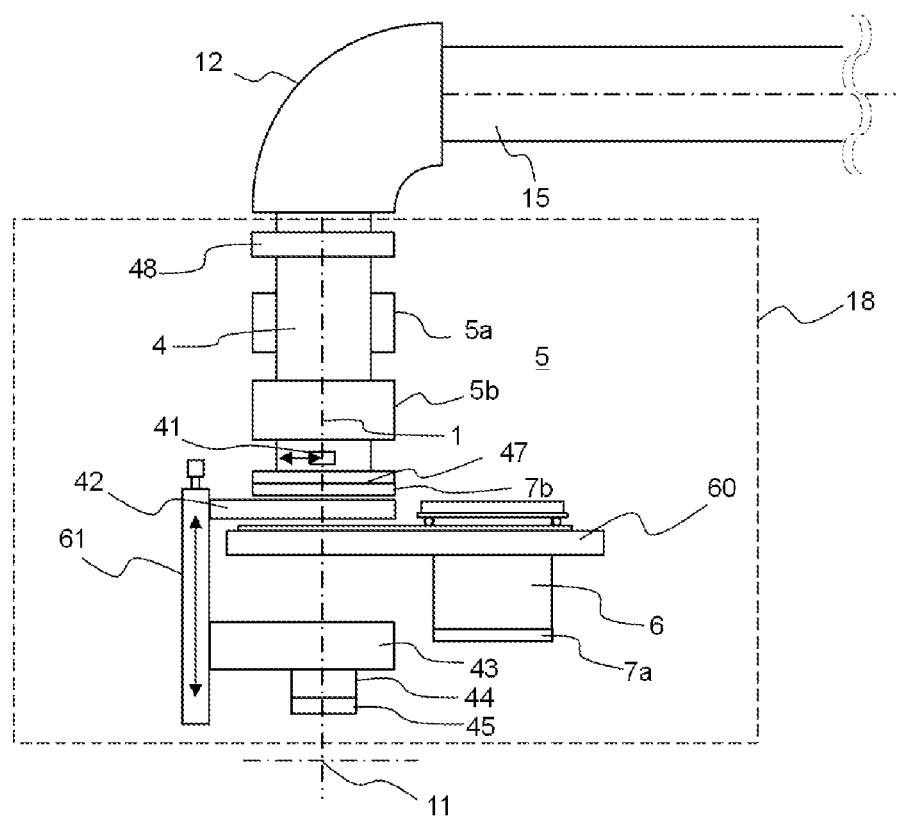
FIG. 3 is a front view showing a configuration of an irradiation unit which is a particle beam therapy system in a case of a broad beam irradiation method according to Embodiment 1 of this invention.

Next, a case where irradiation method is switched from a scanning irradiation method to a broad beam irradiation method will be described. FIG. 3 shows the state of an irradiation unit shown in FIG. 1 in which an irradiation method is switched from a scanning irradiation method to a broad beam irradiation. In a scanning irradiation method, a particle beam therapy system has the configuration such that a vacuum duct for scanning irradiation method 6 is arranged at a position which is close to an irradiation position so as not to enlarge a beam spot size. On the other hand, in a broad beam irradiation method, it is necessary to enlarge an energy width of a particle beam. Therefore, it is necessary to arrange the ridge filter 42 at a position which is away from an irradiation object. In a particle beam therapy system according to EMBODIMENT 1, all of the vacuum ducts for scanning irradiation method 6 which are provided at downstream of the scanning electromagnet 5 are removed so as to evacuate from a position on the beam line 1. As a result, large space can be secured.

FIG. 1 shows the configuration in which the vacuum duct for scanning irradiation method 6 can be separated from the vacuum duct 4 by a flange surface 47 which is provided at downstream of the scanning electromagnet 5. Further, the particle beam therapy system has the configuration such that when the vacuum duct for scanning irradiation method 6 is removed from a flange, by a driving base which receives the vacuum duct for scanning irradiation method 6 and a vacuum duct transfer mechanism 60 having a driving rail, the vacuum duct for scanning irradiation method 6 is slid, and evacuated easily from a position on the beam line 1 so as not to overlap with the beam line 1.

After the vacuum ducts for scanning irradiation method 6 is removed, the vacuum duct connecting flange surface 47 is a final surface, therefore, as shown in FIG. 3, a beam outlet window 7b is attached on the flange surface 47. In space which is generated by sliding the vacuum duct for scanning irradiation method 6 by the vacuum duct transfer mechanism 60, the ridge filter 42 is transferred by a ridge filter transfer mechanism 61 in a direction close to the flange surface 47, raised to a position which is just below the beam outlet window 7b, and installed. In this time, the ridge filter 42 is switched from that for a scanning irradiation method to that for a broad beam irradiation method. Further, the range shifter 43 is transferred up and down as appropriate, and a bolus 44 and a patient collimator 45 are placed as appropriate. Further, when a scanning irradiation method is performed, the scatter 41 which was evacuated from a position on the beam line 1 is transferred to a position on the beam line 1. By performing the above-mentioned, a broad beam irradiation can be performed. By the configuration in which the bolus 44 and the patient collimator 45 are attached to a lower surface of the range shifter 43 by attaching a holder for insertion with a rail, the bolus 44 and the patient collimator 45 can be installed easily. Further, the ridge filter 42 and the range shifter 43 can be inserted by using a linear driving mechanism or a rotary driving mechanism using air or a motor. Further, according to the above-mentioned configuration, the vacuum ducts for scanning irradiation method 6 is evacuated by sliding, however, a method, in which a rotary supporting mechanism is provided and a flange and insertion space are switched by rotating a supporting mechanism, can be realized.

In a case where a vacuum separation surface is not provided at a position which is upper stream than the vacuum duct for scanning irradiation method 6, and the vacuum duct for scanning irradiation method 6 is communicated from upstream, by removing the vacuum duct for scanning irradiation method 6, all of vacuum of beam transport system is broken. In this case, it takes time for increasing a degree of vacuum; therefore, it is preferable such that a gate valve is arranged at a position which is just upstream of the scanning electromagnet 5. The gate valve 48 may be arranged just downstream of the scanning electromagnet 5. When the vacuum duct for scanning irradiation method 6 is removed, by closing the gate valve 48, influence to a degree of vacuum can be suppressed only in an area which is downstream than the gate valve 48. When the gate valve 48 serves a function of a final beam outlet window, it is not necessary to attach the beam outlet window 7b, therefore, switching can be performed in shorter time.

As above-mentioned, according to EMBODIMENT 1, in a broad beam irradiation method, the vacuum duct for scanning irradiation method 6 which is used for a scanning irradiation method is evacuated so as not to overlap with a beam line 1 through which a beam passes, and in vacant space, the ridge filter 42 is transferred in a direction of the beam line so as to arrange. Consequently, the ridge filter 42 can be arranged at a position which is away from an irradiation object, whole of irradiation unit can be formed compactly and a ridge filter which can be easily manufactured can be used.

Embodiment 2

Figure 4:
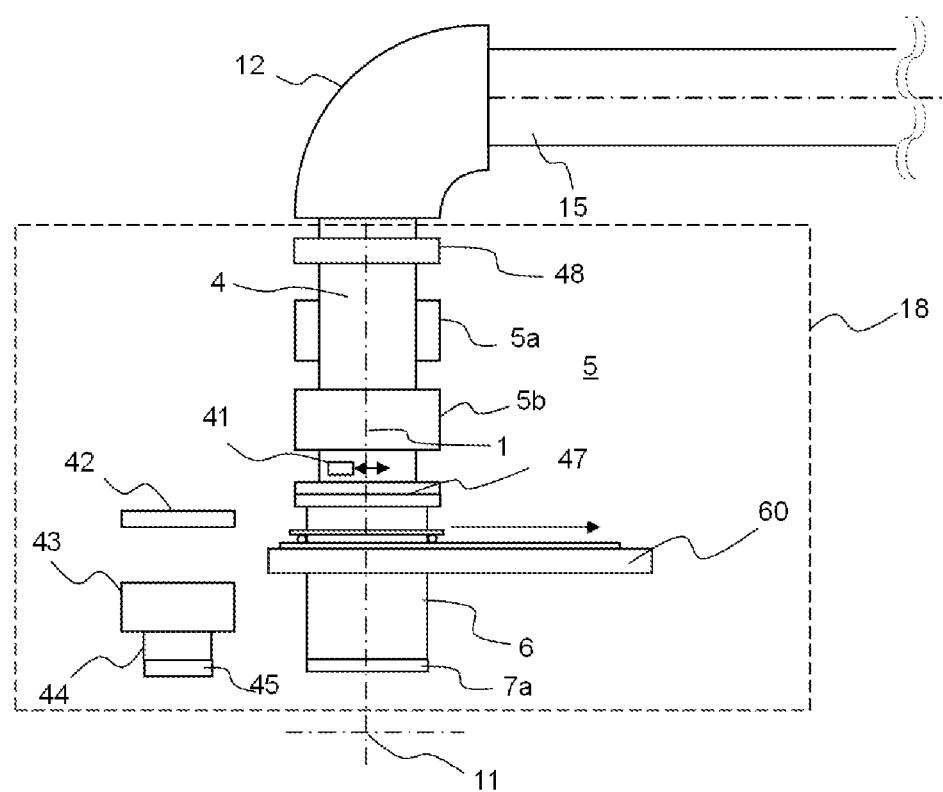
FIG. 4 is a front view showing a configuration of an irradiation unit which is a main unit of a particle beam therapy system in a case of a scanning irradiation method according to Embodiment 2 of this invention.
Figure 5:
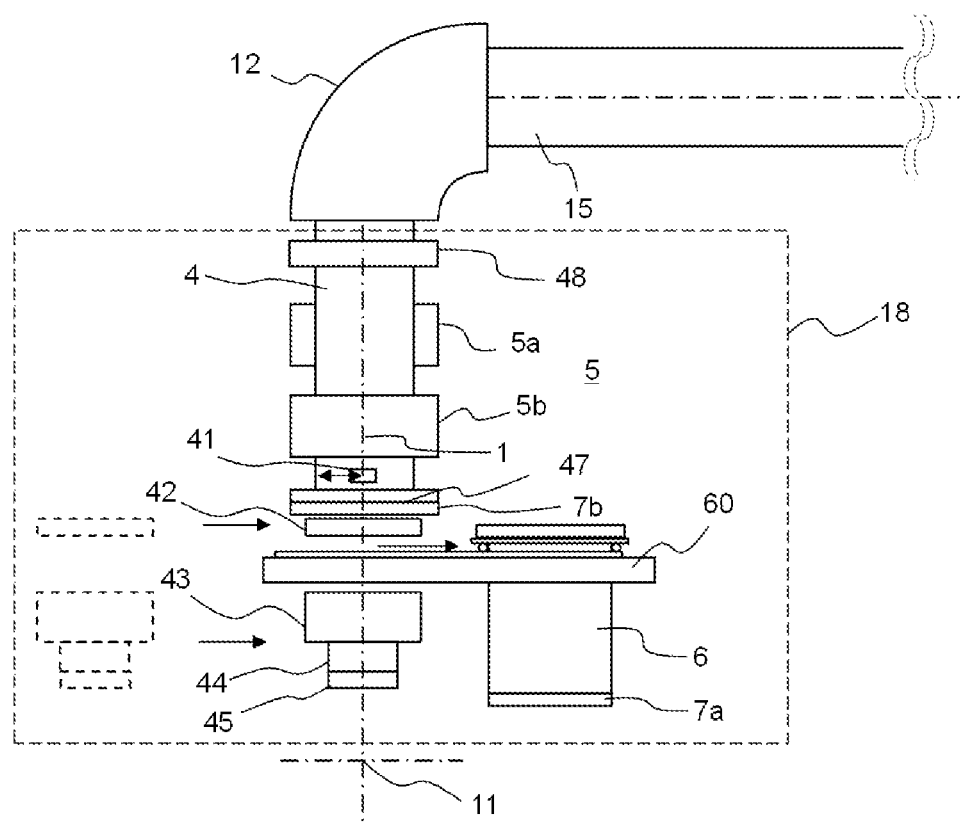
FIG. 5 is a front view showing a configuration of an irradiation unit which is a main unit of a particle beam therapy system in a case of a broad beam irradiation method according to Embodiment 2 of this invention.

FIG. 4 and FIG. 5 are views showing the configuration of an irradiation unit which is a main unit of a particle beam therapy system according to EMBODIMENT 2. FIG. 4 shows the configuration in a case where a scanning irradiation method is performed in a particle beam therapy system according to EMBODIMENT 2. According to EMBODIMENT 1, a scanning irradiation method has the configuration in which a ridge filter is used. In a case where an irradiation is performed by a scanning irradiation method, scattering of a beam of a particle beam is suppressed as much as possible so as to reduce a size of a beam spot at a beam irradiation position. Consequently, in many cases, a particle beam therapy system has the configuration such that a vacuum duct is arranged right up to a beam irradiation position as shown in FIG. 4. In this time, a scatterer 41, a ridge filter 42 and a range shifter 43 are not required; therefore, the scatterer 41, the ridge filter 42 and the range shifter 43 are evacuated so as not to overlap with a beam line 1.

Next, in EMBODIMENT 2, a method in which equipment configuration of a scanning irradiation method is switched to that of a broad beam irradiation method will be described. In a scanning irradiation method, in order to reduce a beam spot size, a particle beam therapy system has the configuration such that a vacuum duct is arranged right up to an irradiation position. However, according to the above-mentioned configuration, there is not any space for arranging a ridge filter, etc. which is used for a broad beam irradiation method. In a case where a ridge filter, etc. is arranged with the arrangement of a vacuum duct for scanning irradiation method 6 as shown in FIG. 4 as it is, a ridge filter is arranged in space at downstream of the vacuum duct for scanning irradiation method 6 (before an irradiation position). Consequently, a distance to an irradiation object is short, as a result, it is difficult to manufacture a ridge filter which can be used in this distance. According to Patent Document 2, space for arranging an apparatus is generated by contracting a gas chamber. However, according to EMBODIMENT 2, a particle beam therapy system has the configuration such that the vacuum duct for scanning irradiation method 6 which is arranged at downstream of a scanning electromagnet 5 is removed and evacuated so as to secure space which is much larger than space disclosed in Patent Document 2.

In FIG. 4, the vacuum duct for scanning irradiation method 6 has the configuration such that the vacuum duct for scanning irradiation method 6 can be separated from a vacuum duct 4 at a flange surface 47 which is downstream of the scanning electromagnet 5. Further, the particle beam therapy system has the configuration such that when the vacuum duct for scanning irradiation method 6 is removed from a flange, by a driving base which receives the vacuum ducts and a vacuum duct transfer mechanism 60 having a driving rail, the vacuum duct for scanning irradiation method 6 is slid and evacuated easily from a position on the beam line 1 so as not to overlap with the beam line 1.

FIG. 5 shows the configuration in which an irradiation method is switched to a broad beam irradiation method in EMBODIMENT 2. After the vacuum duct for scanning irradiation method 6 is removed, a vacuum duct connecting flange surface 47 is a final surface, therefore, as shown in FIG. 3, a beam outlet window 7b is attached on the flange surface 47. In space which is generated by sliding the vacuum duct for scanning irradiation method 6, the ridge filter 42 and the range shifter 43 are inserted. Further, the scatter 41 which was evacuated from a position on the beam line 1 when a scanning irradiation method was performed is transferred to a position on the beam line 1. Further, as appropriate, by attaching a bolus 44 and a patient collimator 45, a broad beam irradiation can be performed. By the configuration in which the bolus 44 and the patient collimator 45 are attached to an lower surface of the range shifter 43 by attaching a holder for insertion with a rail, the bolus 44 and the patient collimator 45 can be installed easily. Further, the ridge filter 42 and the range shifter 43 can be inserted by using a linear driving mechanism or a rotary driving mechanism using air or a motor. Further, according to the above-mentioned configuration, the vacuum duct for scanning irradiation method 6 is evacuated by sliding, however, a method, in which a rotary supporting mechanism is provided and a flange and insertion space is switched by rotating the supporting mechanism, can be realized.

As above-mentioned, according to EMBODIMENT 2, in a broad beam irradiation method, the vacuum duct for scanning irradiation method 6 which is used for a scanning irradiation method is evacuated so as not to overlap with a beam line 1 through which a beam passes, and in vacant space, the ridge filter 42 is inserted. Consequently, the ridge filter 42 can be arranged at a position which is away from an irradiation object, whole of irradiation unit can be formed compactly and a ridge filter which can be easily manufactured can be used.

Embodiment 3

Figure 6:
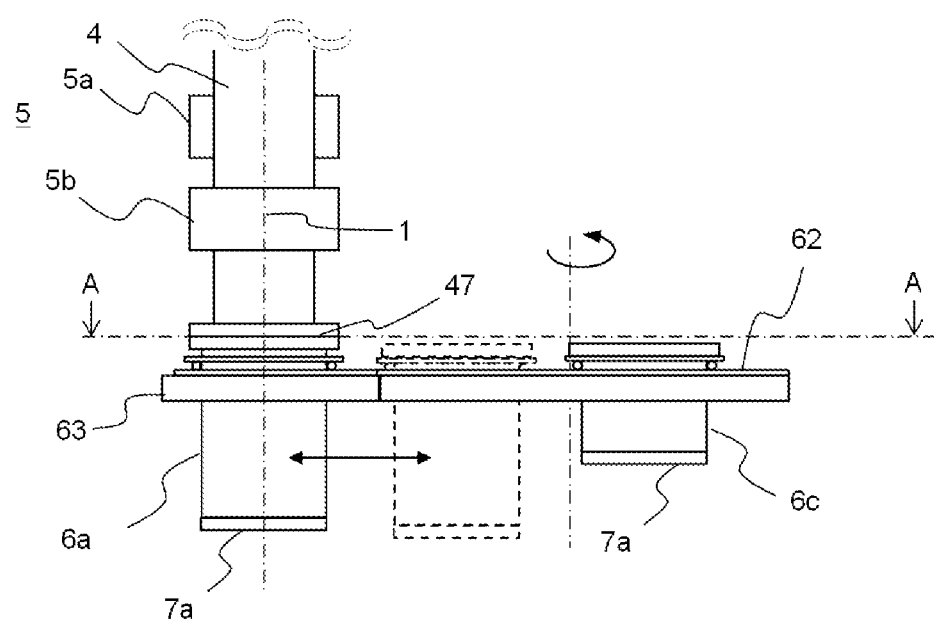
FIG. 6 is a front view showing a configuration of an irradiation unit which is a main unit of a particle beam therapy system in a case of a scanning irradiation method according to Embodiment 3 of this invention.
Figure 7:
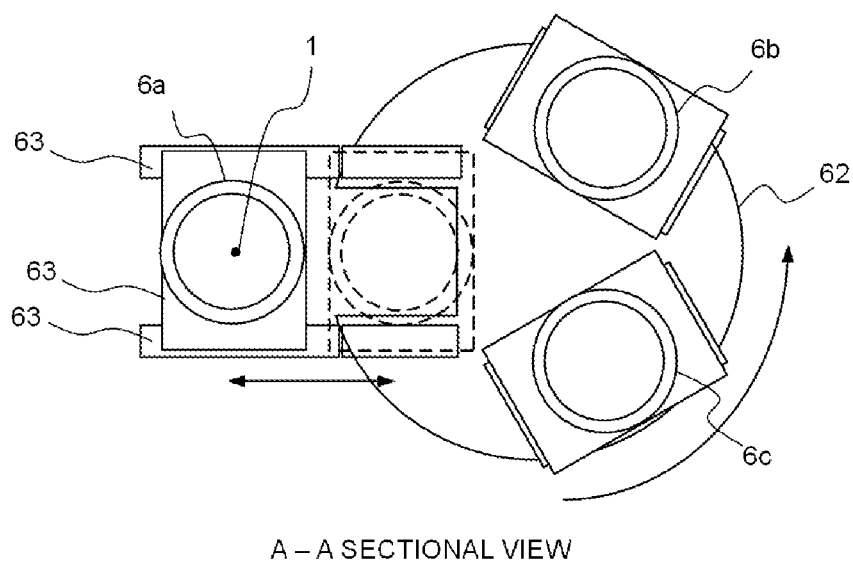
FIG. 7 is a cross-sectional view taken on line A-A of FIG. 6 showing a configuration of a configuration of an irradiation unit which is a main unit of a particle beam therapy system in a case of a scanning irradiation method according to Embodiment 3 of this invention.

FIG. 6 and FIG. 7 are views showing the configuration of an irradiation unit which is a main unit of a particle beam therapy system according to Embodiment 3 of this invention. FIG. 7 is a cross-sectional view taken on line A-A of FIG. 6. According to the configuration of EMBODIMENT 1 and EMBODIMENT 2, in a case of a scanning irradiation method, a position of a beam outlet window is determined by a length of a vacuum duct for scanning irradiation method 6, therefore, a position of the beam outlet window can not be adjusted according to a size of an irradiation object. However, in a case of a scanning irradiation method, a spot size is reduced to be as small as possible, therefore, it is preferable such that a position of the beam outlet window is made to be closer to an irradiation object as much as possible. According to EMBODIMENT 3, the configuration in which a height of the beam outlet window can be changed can be realized.

By referring to FIG. 6 and FIG. 7, an irradiation unit of a particle beam therapy system according to EMBODIMENT 3 will be described. According to EMBODIMENT 3, a particle beam therapy system has the characteristic such that the system comprises a rotating disk type vacuum duct support mechanism 62 for holding a plurality of vacuum ducts for scanning irradiation method 6a, 6b and 6c having a different length. First, in FIG. 6 and FIG. 7, the vacuum duct for scanning irradiation method 6a which is attached on a beam line 1 is removed and slid by a vacuum duct transferring mechanism 63 so as to evacuate to vacant space of the rotating disk type vacuum duct support mechanism 62 for holding the vacuum duct for scanning irradiation method 6a at a position where the position does not overlap with the beam line 1. After that, the rotating disk type vacuum duct support mechanism 62 is rotated so as to set at an angle by which a vacuum duct for scanning irradiation method having a length which is different from that of the vacuum duct for scanning irradiation method 6a, for example, the vacuum duct for scanning irradiation method 6b can be provided. By setting the above-mentioned, by the vacuum duct transferring mechanism 63, the vacuum duct for scanning irradiation method 6b having a different length can be transferred on the beam line 1. By attaching the vacuum duct for scanning irradiation method 6b to a connecting flange surface 47, a height of a beam outlet window 7a can be changed. In FIG. 7, a case where three types of vacuum duct are arranged is described, however, by enlarging a size of rotating disk; a number of types of vacuum duct whose length can be changed can be increased. Further, by providing a ridge filter transfer mechanism 61 which was described in EMBODIMENT 1, after a height of a beam outlet window is changed, a position of a ridge filter and that of a range shifter can be changed according to a height of the beam outlet window.

In EMBODIMENT 3, as a supporting mechanism for holding a plurality of vacuum ducts for scanning irradiation method at a position where a beam line 1 does not overlap is described. In addition to the above-mentioned, as a supporting mechanism for holding a plurality of vacuum ducts for scanning irradiation method at a position where a beam line 1 does not overlap, a length of a vacuum duct can be changed in the same way as that of the above-mentioned, by making the configuration in which a plurality of branching points at a side of evacuation of a vacuum duct transfer mechanism are provided, or making the configuration in which a vacuum duct can be divided in a direction of the beam line 1 so as to provide a vacuum duct transfer mechanism at each dividing unit.

Embodiment 4

As an irradiation unit 18a which is mounted on a rotating gantry 19 shown in FIG. 1, one of irradiation units 18 which were described in the EMBODIMENTs 1 to 3 can be applied. Generally, irradiation of a particle beam is performed while a rotating gantry is stopped. In a case where one of irradiation units 18 which were described in EMBODIMENTs 1 to 3 is mounted on a rotating gantry, it is preferable from a view point of operation such that transferring operation of a vacuum duct is performed at zero degree of gantry angle (an angle where an irradiation unit is arranged vertically).

REFERENCE CHARACTERS

1: beam line
4, 15: vacuum duct
6, 61, 6b, 6c: vacuum duct for a scanning irradiation method
5, 5a, 5b: scanning electromagnet
7a, 7b: beam outlet window
11: isocenter
12, 13: bending electromagnet
14: accelerator
17: beam transport unit
18, 18a, 18b: irradiation unit
19: rotating gantry
41: scatterer
42: ridge filter
43: range shifter
44: bolus
45: patient collimator
47: flange surface
48: gate valve
60, 63: vacuum duct transfer mechanism
61: ridge filter transfer mechanism
62: rotating disk type vacuum duct support mechanism

The invention claimed is:

1. A particle beam therapy system comprising
an irradiation unit having a scanning electromagnet for irradiating an irradiation object by scanning a particle beam which travels in a vacuum duct and a beam outlet window from which a particle beam comes out from the vacuum duct to the atmosphere,
wherein the irradiation unit has the configuration such that a vacuum duct is provided which can be divided by a flange surface at an irradiation object side of the scanning electromagnet,
in a case where a vacuum duct for a scanning irradiation method is provided at an irradiation object side of the flange surface, a ridge filter for a scanning irradiation method is provided at the irradiation object side of the vacuum duct for a scanning irradiation method,
in a case where the vacuum duct for a scanning irradiation method is moved so as not to overlap with a beam line of the particle beam, the ridge filter for a scanning irradiation method is removed and a ridge filter for a broad beam irradiation method can be provided in space which is on a beam line of a particle beam and where the vacuum duct for a scanning irradiation method was provided before it was moved.

2. A particle beam therapy system according to claim 1, wherein the irradiation unit comprises a ridge filter transfer mechanism by which a ridge filter is moved to a beam line direction of the particle beam,
in a case where the scanning irradiation method vacuum duct is moved so as not to overlap a beam line of the particle beam,
in place of the ridge filter for a scanning irradiation method which is provided at the ridge filter transfer mechanism, the ridge filter for a broad beam irradiation method is provided at the ridge filter transfer mechanism, the ridge filter for a broad beam irradiation method is moved to close to a direction of the flange surface and is provided.

3. A particle beam therapy system according to claim 1, wherein a gate valve is provided at a position which is upper stream than the flange surface of the vacuum duct.

4. A particle beam therapy system according to claim 1, wherein the beam outlet window is provided on the flange surface in a case where the vacuum duct for a scanning irradiation method is moved so as not to overlap a beam line of the particle beam.

5. A particle beam therapy system according to claim 1, further comprises a plurality of the vacuum ducts for a scanning irradiation method whose length are different, a holding mechanism which holds the plurality of the vacuum ducts for a scanning irradiation method at a position which does not overlap the beam line and a vacuum duct transfer mechanism by which one of the plurality of the vacuum ducts for a scanning irradiation method can be moved from the holding mechanism to the beam line.

6. A particle beam therapy system according to claim 1, wherein the irradiation unit is mounted on a rotating gantry.

* * * * *